United States Patent [19]

Richling: Bernd et al.

[11] Patent Number: 5,429,605

[45] Date of Patent: Jul. 4, 1995

[54] MICROBALLOON CATHETER

[75] Inventors: Richling: Bernd, Vienna, Austria; Ivan Sepetka, Redwood City; Uriel H. Chee, San Carlos; Liem Ho, Mountain View; Phong Pham, Fremont, all of Calif.

[73] Assignee: Target Therapeutics, Inc., Fremont, Calif.

[21] Appl. No.: 188,382

[22] Filed: Jan. 26, 1994

[51] Int. Cl.⁶ .......................................... A61M 29/00
[52] U.S. Cl. ......................................... 604/96; 606/194
[58] Field of Search ................................ 604/96–103; 606/192–195

[56] References Cited

U.S. PATENT DOCUMENTS

| | | | |
|---|---|---|---|
| 4,597,755 | 7/1986 | Samson et al. | 604/96 |
| 4,771,776 | 9/1988 | Powell et al. | 604/96 |
| 4,775,371 | 10/1988 | Mueller, Jr. | 606/192 X |
| 4,981,478 | 1/1991 | Evard et al. | 606/194 X |
| 5,192,295 | 3/1993 | Danforth et al. | 606/194 |
| 5,192,296 | 3/1993 | Bhate et al. | 604/96 X |
| 5,300,025 | 4/1994 | Wantink | 606/194 X |
| 5,304,135 | 4/1994 | Shonk | 606/194 X |

*Primary Examiner*—C. Fred Rosenbaum
*Assistant Examiner*—Frank Wilkens, III
*Attorney, Agent, or Firm*—Morrison & Foerster

[57] ABSTRACT

This invention is a microballoon tipped catheter. The catheter has a shaft which is of varying flexibility with the most flexible portion towards the distal tip. The balloon, located near the distal tip of the catheter, is typically of an elastic material, is quite flexible in its own right when deflated, and is quite small. The catheter shaft has a main lumen extending from the proximal end to the distal end so to allow the use of a guidewire in placing the catheter's distal tip in remote regions of the vasculature and for delivery of drugs, diagnostics, and other biologics to those regions. The catheter shaft has a wall that desirably is of a multilayer construction. The wall preferably includes an independent lumen, which may be formed from a small diameter tubing that is placed between layers of the wall, for the inflation and deflation of the microballoon. The inflation lumen proceeds from the proximal end of the catheter and terminates near the distal end of the catheter but within the microballoon. This catheter is especially useful in treating disease within the high pressure vessels of the brain with drugs or other therapeutic agents and permits temporary blockage of blood flow and thereby allow better absorption of those active agents.

12 Claims, 4 Drawing Sheets

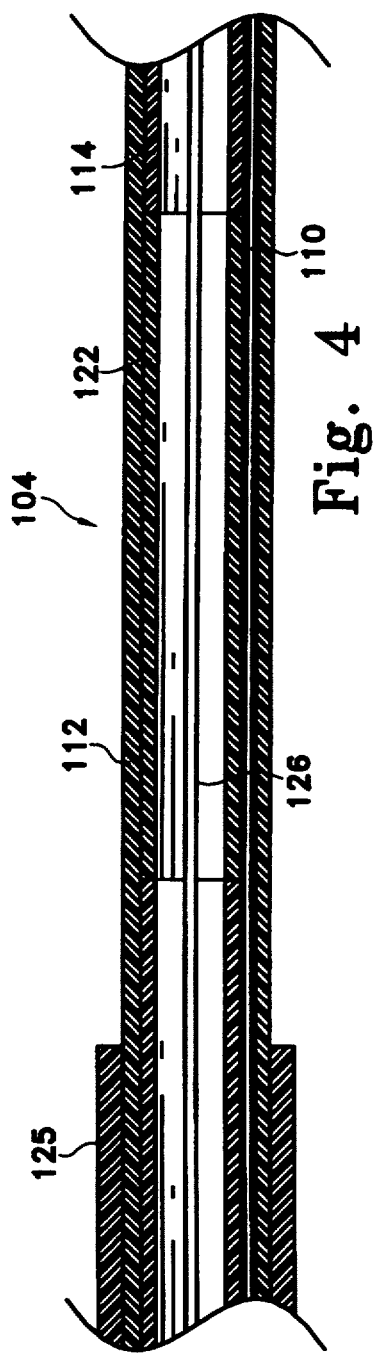
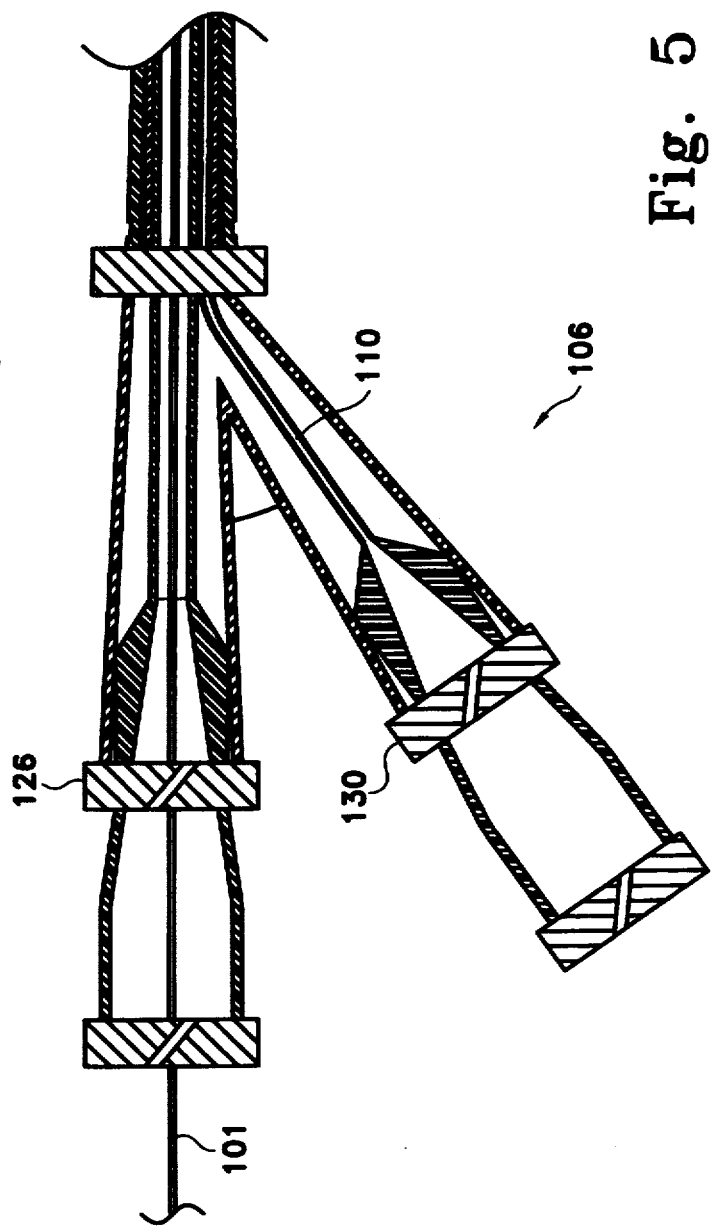
Fig. 4
Fig. 5

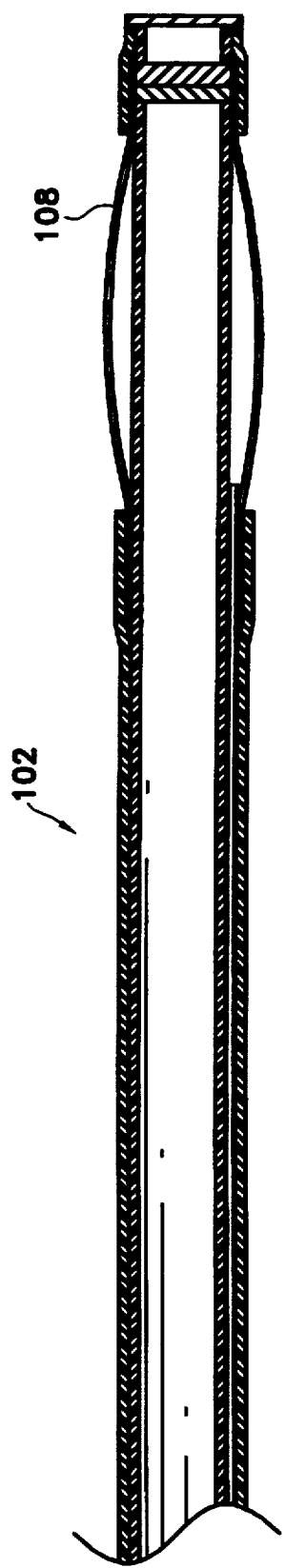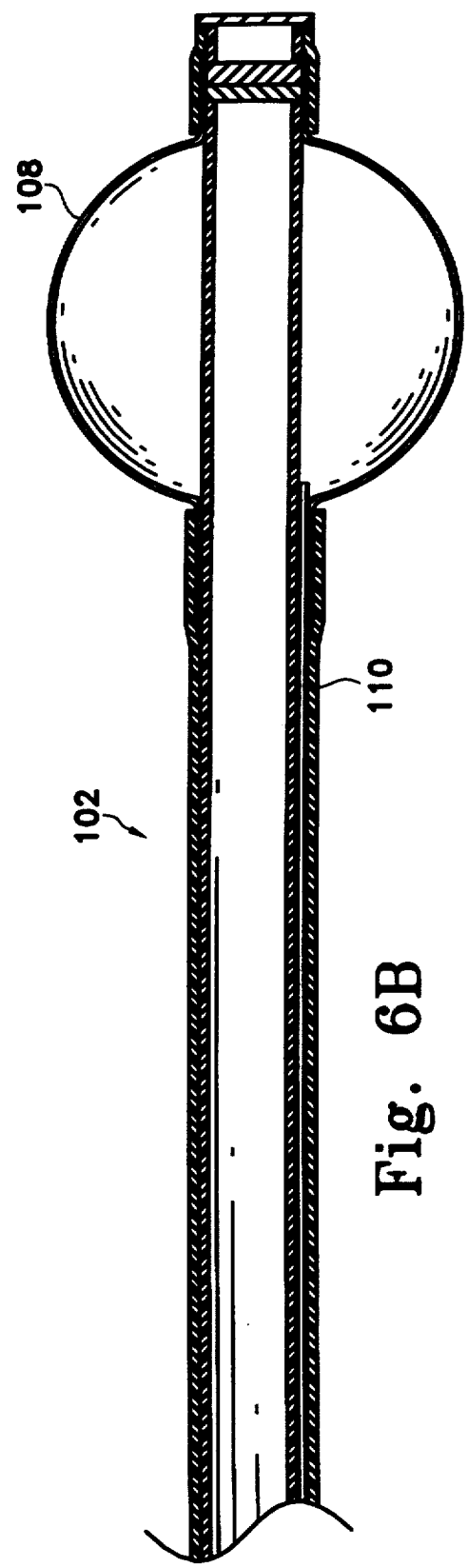

MICROBALLOON CATHETER

FIELD OF THE INVENTION

This invention is a microballoon tipped catheter. The catheter has a shaft which is of varying flexibility with the most flexible portion towards the distal tip. The balloon, located near the distal tip of the catheter, is typically of an elastic material, is quite flexible in its own right when deflated, and is quite small. The catheter shaft has a main lumen extending from the proximal end to the distal end so to allow the use of a guidewire in placing the catheter's distal tip in remote regions of the vasculature and for delivery of drugs, diagnostics, and other biologics to those regions. The catheter shaft has a wall that desirably is of a multilayer construction. The wall preferably includes an independent lumen, which may be formed from a small diameter tubing that is placed between layers of the wall, for the inflation and deflation of the microballoon. The inflation lumen proceeds from the proximal end of the catheter and terminates near the distal end of the catheter but within the microballoon. This catheter is especially useful in treating disease within the high pressure vessels of the brain with drugs or other therapeutic agents and permits temporary blockage of blood flow and thereby allow better absorption of those active agents.

BACKGROUND OF THE INVENTION

Balloons on catheters are used for a variety of purposes. In large vessels, one such use is angioplasty. Angioplasty is a method for treating a wide variety of vascular diseases. In particular, it has been used extensively for opening stenoses in coronary arteries and, increasingly, in other parts of the vascular system.

One of the more well known and widely practiced forms of angioplasty makes use of a dilatation catheter which has an inflatable balloon at is distal end. Using fluoroscopy, the physician guides the catheter through the vascular system until the balloon is properly positioned. By applying a fluid through the separate inflation lumen, the balloon is inflated. The balloon's inflation causes the artery to stretch and presses the lesion or stenose into the artery wall, thereby reestablishing after deflation of the balloon, increased blood flow through the artery.

In order to treat very tight stenoses, i.e., those having small openings, increasingly small catheter diameters are desirable. Significantly more flexible catheters are also desired in that otherwise very tight areas of stenosis will not be approachable. Although flexible and narrow of diameter, a good catheter must also be easily introduced and easily advanced through the tortuous path of the vascular system.

There are a variety of dilatation catheter types. Many use multiple lumens. For instance, a catheter may use a separate guidewire lumen so that a guidewire can be used to establish the path to the stenosis. The catheter may then be fed over the guidewire until the balloon is positioned over the stenosis. The catheter obviously has a separate lumen to allow introduction of and removal of fluid for the balloon.

Other catheter designs include those which act as their own guidewire, thereby eliminating the need for a separate guidewire lumen. Elimination of the need for the separate lumen means that the profile of the catheter can be somewhat smaller. Typical of such integral designs are U.S. Pat. No. 4,606,347, to Fogarty et al., which shows a catheter having an evertable and inflatable balloon at its distal tip. The distal tip of the catheter is placed near the stenosis to be treated. The balloon is extended beyond the distal tip to a position within the stenosis and then inflated to press the lesion back into the wall of the vessel. The balloon contains a passageway in the middle having a plug of some elastomeric material through which a guidewire may be placed. The plug retains the pressure of the fluid on the balloon, whether the guidewire is present or not.

Another "over-the-wire" catheter is shown in U.S. Pat. No. 5,085,636, to Burns. The Burns device utilizes a balloon having a port for introducing fluid into the balloon and simultaneous device for not allowing fluid to pass through the catheter when a guidewire is present in the vicinity of the balloon. The fluid seal is distendible and does not allow fluid past the guidewire.

The U.S. patent application Ser. No. 07/650,808, filed Feb. 5, 1991 entitled "Single Lumen Low Profile Valved Balloon Catheter" discloses a single lumen balloon catheter having a catheter using a flexible guidewire which extends axially through the lumen beyond the open end of an intermediate balloon segment. The guidewire is axially movable within the lumen and has two discrete portions of different diameters. The first diameter, distal on the guidewire, is smaller that a second more proximal diameter on the guidewire. The larger guidewire meshes with the diameter of the lumen just proximal of the balloon thereby sealing it on the proximal end. Simultaneously at the distal end of the balloon a valve member mounted on the guidewire blocks the distal opening of the catheter.

In addition to angioplasty, catheters are also used to deliver therapeutics or diagnostic agents to internal target sites. For example, in angiography, catheters are used to deliver a radiopague agent to a target site within a blood vessel, to allow radiographic viewing a the vessel and blood flow characteristics near the release site. For treatment of localized diseases such as solid tumors, catheters are used to introduce therapeutics agents to the target site at a relatively high concentration with concomitant reduction of delivery of the drug to nontarget sites.

Often the target site chosen is within a tissue, such as the brain, liver, or kidney. Such a target site requires catheter placement along a tortuous path through small vessels or ducts such as arterial vessels or biliary ducts.

One catheter used for accessing an internal body site along a small diameter vessel path is shown in U.S. Pat. No. 4,813,934, to Engelson et al. The catheter device described there is one that has a distal end inflatable balloon and a guidewire extending distally of the balloon. The balloon is alternatively inflated and deflated by fluid infusion into the catheter by manipulation of the guidewire. The balloon is inflated as a means to hydrodynamically carry the tip of the catheter quickly along the vascular lumen. In catheter placement operation, the catheter is advanced along the vessel path toward the selective target site. When the catheter tip reaches a branch point at which the path follows the larger diameter vessel, the guidewire is moved to a position which blocks the catheter aperture, and fluid inflates that balloon. The catheter is then carried by hydrodynamic flow into the larger diameter vessel. When the catheter tip encounters a branch point at which the desired path follows the small diameter of the two vessels, the balloon is deflated and the guidewire is manipulated to orient the wire for movement into the small vessel.

Although the prior art shows a number of designs for over-the-wire balloon catheters, none of the prior art shows a device having a microballoon tip and separate inflation lumen located among the polymeric layers forming the wall of the catheter lumen.

SUMMARY OF THE INVENTION

This invention is a multi-lumen microballoon catheter assembly having a lengthy catheter body, with multi-layer polymeric walls (optionally with fibrous stiffening within the layers) where the catheter body has a main lumen with a proximal end and an open distal end. The catheter body is increasingly more flexible towards the distal tip and has a balloon section just proximal of that distal tip. The balloon segment or section includes an inflatable balloon member, the interior of which is in fluid communication with an inflation lumen. The inflation lumen is desirably located between the layers of the catheter body making up the catheter body and extends from the interior of the inflatable balloon to the proximal end of the catheter assembly. The invention optionally includes a flexible guidewire extending axially through the main lumen beyond the open end, the guidewire being axially movable within the lumen. Preferably, the catheter body section is a multilayered, polymeric tubing that does not kink, "accordion", or stretch upon application of axial force on the guidewire. The most preferred combination of materials includes a slippery material as the inner and/or outer surface of the catheter body section.

The catheter may be of a very small diameter or low profile and consequently is quite flexible in its operation.

BRIEF DESCRIPTION OF THE DRAWINGS

FIG. 4 shows a close up, side view, cross-section of the mid-section of the catheter assembly of this invention.

FIG. 5 shows a close up, side view, cross-section of the proximal section of the catheter assembly of this invention.

FIGS. 6A and 6B show side views of the balloon section, respectively, as deflated and as inflated.

DESCRIPTION OF THE INVENTION

Figure 1:
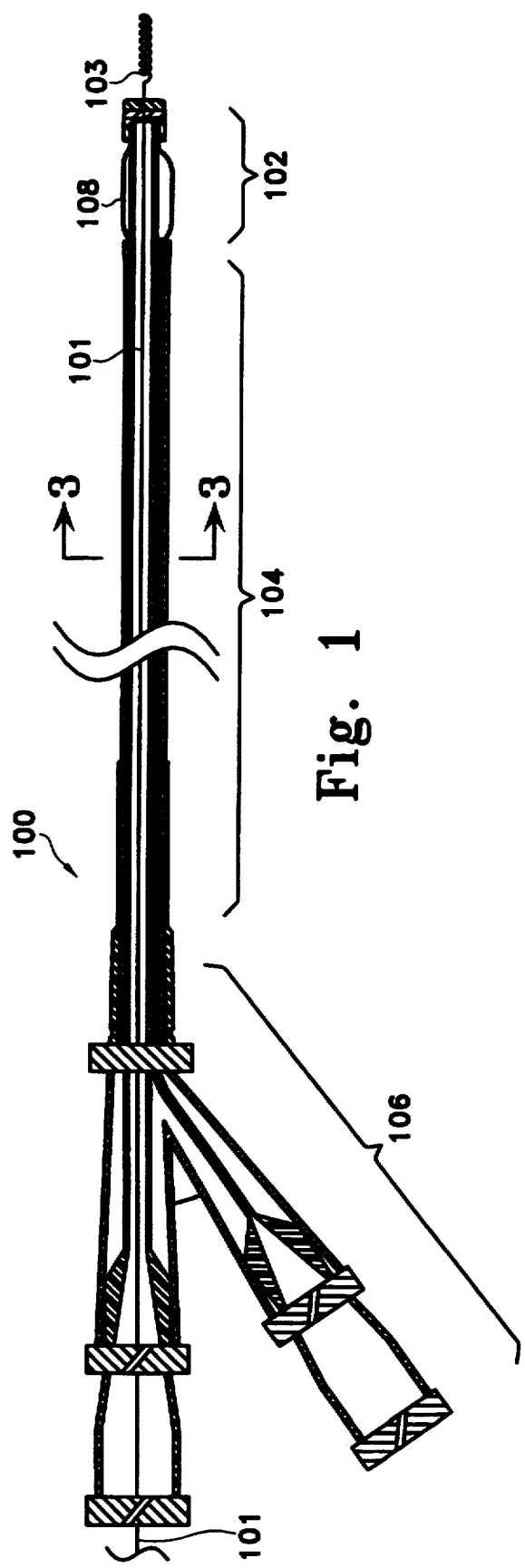
FIG. 1 is a side view of a catheter assembly made according to this invention.

FIG. 1 shows a side view of a catheter assembly, generally designated (100), made according to one embodiment of the invention. The catheter assembly (100) comprises a elongate tubular member with a balloon section (102) at the distal end of the catheter, a body section (104) proximal of the balloon section (104), and a proximal section (106). The catheter assembly (102) is designed for operation in combination with a flexible guidewire (101), preferably with a bendable guide tip (103)that is often a coil, which guidewire is used to guide the catheter assembly (102) along the complicated and tortuous path to a target site within the body. The design of the guidewire (101) may be of any convenient design which allows manipulation of the combined catheter and guidewire to the desired site. The overall length of the catheter assembly is typically between 30 cm. and 175 cm. depending upon the portion of the body to be accessed by the catheter and the chosen body access site. For instance, if the brain is the site and the femoral artery is the access site, the length may be in the higher regions of the noted range. If the access is through the neck, the catheter assembly (100) may be significantly shorter.

Figure 2:
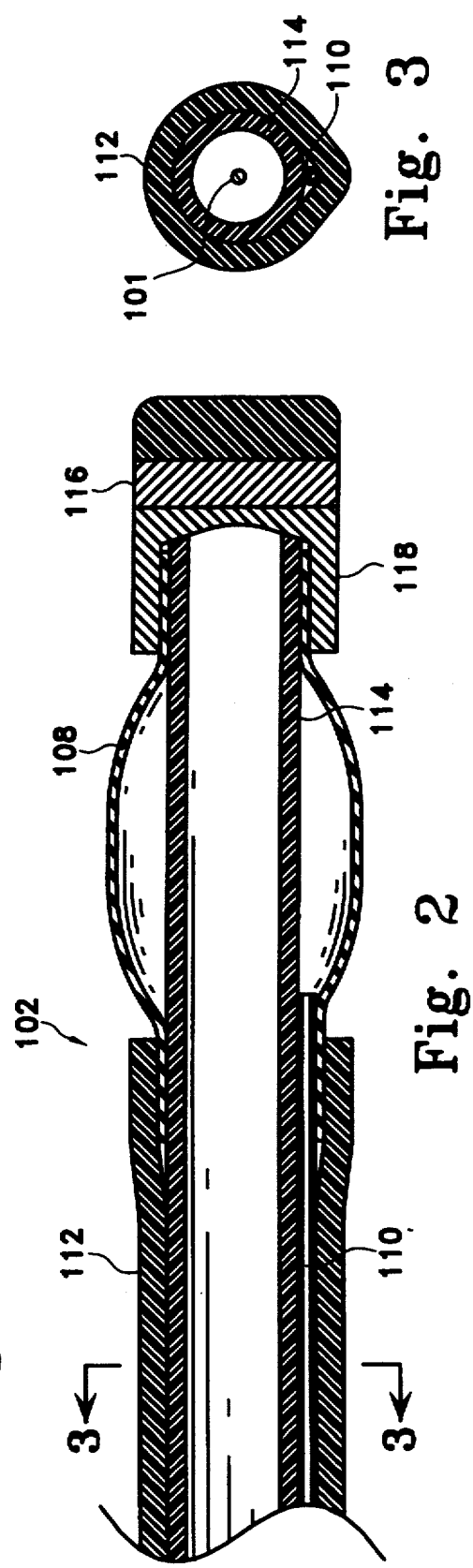
FIG. 2 shows a close up, side view, partial cross-section of the balloon section of the catheter assembly of this invention.

FIG. 2 shows a partial cross section of the balloon section (102) of the catheter assembly. The balloon section includes a balloon (108) in open fluid communication with a an inflation tube (110). The inflation tube (110) is typically of a material which has sufficient radial strength to remain open during the deployment of the catheter. For instance, a polytetrafluoroethylene or high density polyethylene tubing having, e.g., an inner diameter of 0.004" and an outer diameter of 0.008" is sufficiently strong and of sufficiently large flow capacity to allow reasonable inflation and deflation times during that deployment. Both smaller and modestly larger tubing, for instance, tubing having outer diameters between 0.003" and 0.010" are suitable.

The balloon (108) itself desirably is elastomeric. The balloon (108) should not be merely inflatable in the variations used in very narrow vasculature since it will be difficult to fold an inflatable balloon of, e.g., polyethylene, to a small enough diameter to be effective in passing te distal tip of the catheter assembly through that vasculature. Although the design described here is suitable for any size of catheter, for use in very small diameter portions of the vasculature, the axial length of the balloon is about 2 mm to 10 mm. The nonexpanded diameter is 0.035" to 0.050" for neurosurgical devices and up to 0.085" for other services. The elastomeric balloon (108) is preferably of a material such as natural and synthetic rubbers, silicones, etc. Suitable adhesives may be used to seal the balloon (108) against the outer tubing (112) and the inner tubing (114). Both the inner (114) and outer tubing (112) in this balloon section is preferably of a very flexible material such as low density polyethylene, certain silicones, and polyurethanes. Of course, a lubricous coating over the balloon (108) and the inner surface of the inner tubing (114) as well as the outer surface of the outer tubing (112) is useful in deploying the catheter with ease and removing the balloon once the procedure is complete.

The balloon section (102) is the most flexible portion of the catheter assembly (excepting, perhaps, the balloon itself) and typically comprises about 5% to 35% of the overall length of the catheter assembly (100).

The balloon section (102) may have on or more radiopaque markers (116) of platinum or gold or other such known materials. The markers may also be placed on the proximal side of the balloon (108). It may be observed that the distal marker (116) is mounted on a short section of the outer tubing (118) which section (118) serves to seal the balloon (108) and terminate the catheter assembly.

Figure 3:
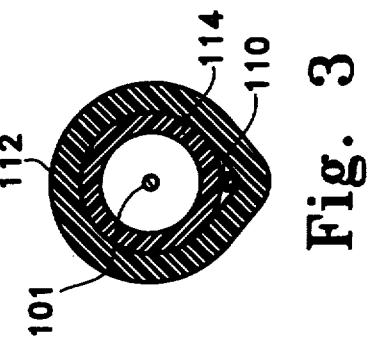
FIG. 3 shows a close up, end view, cross-section of the balloon section of the catheter assembly of this invention.

FIG. 3 shows in cross section the inflation tube (110), inner tubing (114), and outer tubing (112).

FIG. 4 shows the body section (104) located just proximal of the balloon section (102) discussed above and located distal of proximal section (106), which proximal section (106) will be discussed below.

The body section (104) typically makes up 65% to 95% of the total length of the catheter assembly as is shown in FIG. 1. This body section (104) is generally made up in the manner shown in FIG. 3, having outer tubing (112) and a number of inner-tubing sections such as distal section (114) inner-midsection (122) and proximal inner-section (124). The inflation tube (110) may also be seen exterior to the collection of inner-tubes and interior to the outer tube at (112). The number of section of inner-tubing materials may vary depending upon the use to which the catheter is to be placed. The number may be as few as two or as many as six or more. The various sections are typically arranged so that the most flexible is also most distal. The next most flexible is more proximal, and so forth. It is also within the purview of this invention that the various sections of the inner-tubing may be of varying flexibility. That is to say that a section may be concentrically coextruded using two materials or the components may be otherwise joined together so that the distal flexibility of the inner-tubing is enhanced as compared to the proximal flexibility of that same tubing section.

As has been noted elsewhere, the outer-tubing (112) may be a single length of relatively flexible tubing, such as low-density polyethylene, or silicone, which extends from the distal regions of the balloon section (102) to the proximal section (106) (as shown in FIG. 1). Although not described here in great detail, it is contemplated that the outer tubing may also comprise a series of tubing materials. For instance, the more proximal end of the outer tubing may comprise a stiff polymer and the more distal end may comprise a much less stiff material.

It is quite desireable that the more proximal of the inner-tubes (124) be relatively stiff and made up of polypropylene or high-density polyethylene. Other materials such as highly cross-linked silicones, polyesters such as NYLON, polyvinylchloride, high molecular weight polyurethanes, and even various polyimides are also suitable for this proximal inner-tubing (124). Other suitable materials which include a measure of lubricity are polysulfides and polyfluorocarbons. Suitable polyfluoroethylenes include polytetrafluoroethylene, fluoroethylene copolymers having perfluoroalkoxy groups, copolymers of tetrafluoroethylene, hexafluoropropylene, and copolymers of ethylene and tetrafluoroethylene. Most preferred are copolymers of tetrafluoroethylene and hexafluoroethylene. Generally speaking, the stiffness of the proximal inner-segment (124) is to provide a large measure of "pushability" when the catheter is deployed deep within the body.

The midsection inner-member (122) may be made of similar material but either has a thinner tubing wall or is of a material chosen to be less stiff. As the catheter is inserted into the body, the more distal regions of the catheter must be strong but not as strong as the proximal sections and must be able to be twisted without significant distortion of the overall assembly.

The most distal of the inner-tubing sections (114) is again of a material which is more flexible—either by choice of tubing wall thickness or by choice of material—to be more flexible than its next more proximal neighbor. The inner tubing (114) may be of a material such as low density polyethylene, silicones, and polyurethanes.

Ad additional stiffener tube (125) may be added to the exterior of the outer tubing (112) if so desired. Since it is quite proximal on the catheter assembly, it is typically formed of quite stiff materials, often with the addition of a fibrous adjunct embedded within the walls of the stiffener tube.

Other materials of construction will be apparent to one or ordinary skill in this medical design area once the concepts discussed here are appreciated. Reference is made to U.S. Pat. No. 4,739,768, to Engelson, the entirety of which is incorporated by reference, for a description of a device similar to this one without the presence of a balloon (108) and inflation tubing (110).

Inflation tubing (110) was described above in the discussion relating to FIGS. 2 and 3. The inflation tubing passes through the region between the collection of inner-tubing members (e.g., 114, 122, and 124) and outer-tubing (112). A coating of a lubricant such as those described in U.S. Pat. Nos. 4,722,906, 4,973,493, 4,979,959, and 5,002,582 and others of known efficacy may be applied both to the interior of the main lumen (126) or to the exterior surface of outer-tubing (112) or to both.

In general, each of the tubing members discussed herein has a wall thickness between 0.002 inches and 0.006 inches. Typically, the combined wall thickness of the tubes is less than about 0.010 inches. It is desireable that the guidewire (101) in FIG. 1 have a clearance of at least 0.002 inches.

FIG. 5 shows the proximal section (106) of the catheter assembly. The proximal section (106) is a typical "Y" fitting which is adapted in such a way that the straight-through (121) portion allows sealing of the proximal extension of the mid-section tubing (104) and allows the guidewire (101) free and unconstrained access to without the catheter assembly. The sidearm (130) is adapted to accept and seal the proximal section of the inflation lumen (110). The proximal section must be of a configuration which allows removal of the guidewire (101) after final deployment of the catheter assembly distal tip at the selection site. Upon such deployment and removal of the guidewire, the balloon is inflated using the side arm (130), and the diagnostic, drug, or other biologic is introduced through the straight section (128) of the proximal section (106). Certain bushings, wipers, and the like to prevent exit of body fluids from the catheter assembly have been excluded from this discussion and form the drawings for ease and clarity of explanation.

FIG. 6A shows, again, the balloon section (102) of the inventive catheter having an elastomeric balloon (108) in deflated condition.

FIG. 6B shows that same balloon section with the elastomeric balloon (108) inflated.

Figure 7A:
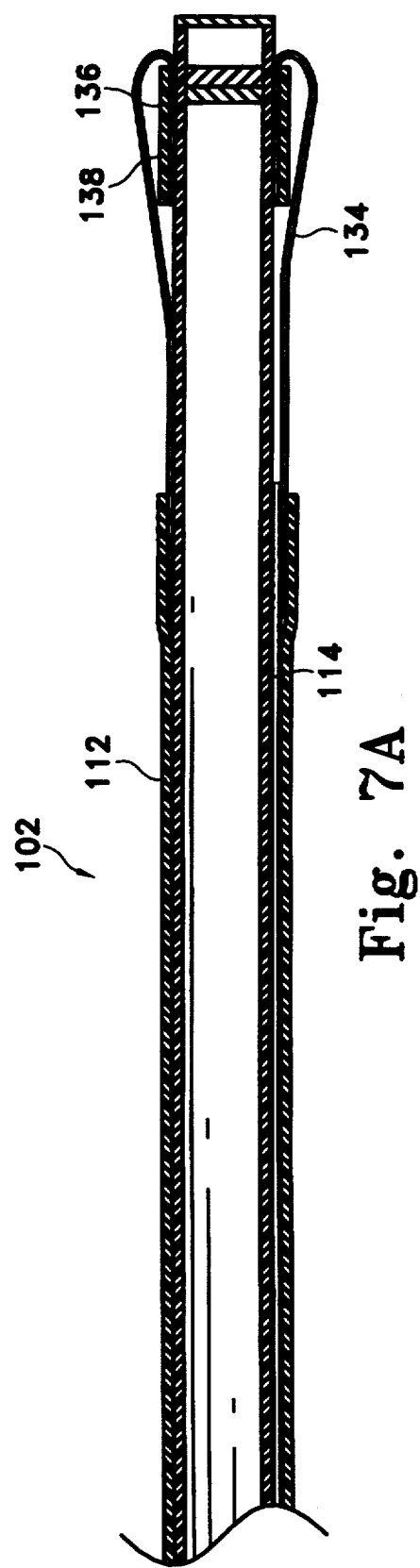
FIGS. 7A and 7B show side views of a second variation of the balloon section, respectively, as deflated and as inflated.

FIG. 7A shows a variation of the balloon section (102) in which the elastic balloon (134) is of a slightly different configuration than that shown in FIGS. 1, 2, 6A, and 6B. In this variation, balloon (134) is, at its proximal end, very similar in configuration and mounting to that shown in the Figures discussed above. However, at its distal end, the balloon reverses itself and the reverse section (136) is placed beneath a filler junction (138). This filler junction may comprise a material such as is found in the outer-tubing (112) and suitable solvent or adhesive to adequately seal balloon (134) against both the inner-tubing (114) and the other components making up the filler junction (138).

Figure 7B:
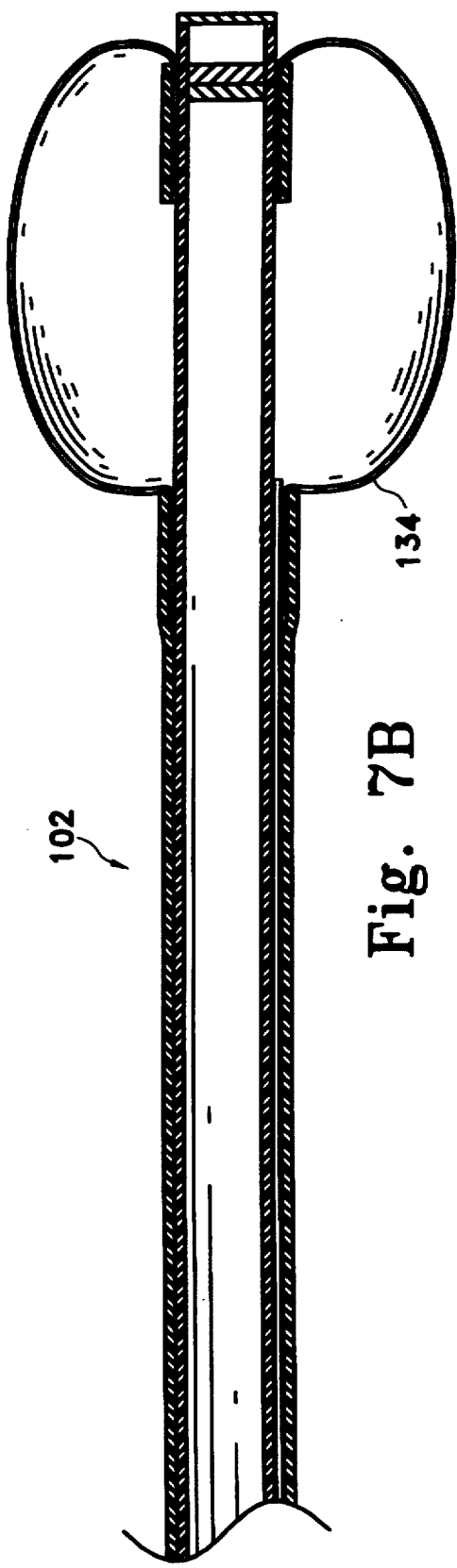

FIG. 7B shows the balloon section (102) depicted in FIG. 7A as the balloon (134) is inflated.

It should be noted that the overall diameter of the catheter at the proximal end of the balloon section is typically in the range of 0.015 inches and 0.040 inches. Consequently, the outer diameter of the inflated balloon is usually no more than about 0.275" for a typical neurovascular application.

Many alterations and modifications may be made by those of ordinary skill in the art without departing from the spirit and scope of this invention. The illustrated embodiments have been shown only for purposes of clarity. The examples should not be taken as limiting the invention as defined by the following claims, which claims include all equivalents, whether those equivalents are now or later devised.

I claim as my invention:

1. A balloon catheter assembly comprising a catheter body having proximal and distal ends; a main lumen extending between those proximal and distal ends said main lumen defined by inner and outer tubes which proximally of an inflatable and deflatable balloon; an inflation tube positioned between the inner and outer tubes and extending between the proximal end of the catheter body and terminating in an inflatable and deflatable balloon; and said inflatable and deflatable balloon having proximal and distal ends and an inner chamber which balloon is in fluid communication only with the inflation tube, said balloon disposed in the distal region of the catheter body.

2. The catheter assembly of claim 1 where the catheter body is progressively more flexible towards the catheter body distal end.

3. The catheter assembly of claim 1 where the balloon is elastomeric.

4. The catheter assembly of claim 2 where the balloon is elastomeric.

5. The catheter assembly of claim 1 where the inner tube comprises two to four discrete sections, each having a different flexibility, arranged in an order such that the discrete sections have increasing flexibility towards the distal end.

6. The catheter assembly of claim 1 where the outer tube is a single length of tubing.

7. The catheter assembly of claim 5 where the outer tube is a single length of tubing.

8. The catheter assembly of claim 1 additionally comprising a guidewire axially moveable within the main lumen.

9. The catheter assembly of claim 8 where the guidewire additionally comprises a bendable guide tip.

10. The catheter assembly of claim 1 additionally comprising at least one radiopaque marker located in the distal region of the catheter assembly.

11. The catheter assembly of claim 10 where at least one radiopaque marker is distal of the balloon.

12. The catheter assembly of claim 1, for use in accessing a site within the brain, wherein the catheter assembly is less than 175 cm. in length.

* * * * *

UNITED STATES PATENT AND TRADEMARK OFFICE
CERTIFICATE OF CORRECTION

PATENT NO. : 5,429,605
DATED : July 4, 1995
INVENTOR(S) : Richling et al.

It is certified that error appears in the above-indentified patent and that said Letters Patent is hereby corrected as shown below:

On the Title Page, item [19], should be RICHLING et al.
Column 7: item [75], should be Bernd Richling,
Claim 1, should read as follows:

A balloon catheter assembly comprising a catheter body having proximal and distal ends; a main lumen extending between those proximal and distal ends said main lumen defined by inner and outer tubes which are in contiguous, approximately coaxial relationship proximally of an inflatable and deflatable balloon; an inflation tube positioned between the inner and outer tubes and extending between the proximal end of the catheter body and terminating in an inflatable and deflatable balloon; and said inflatable and deflatable balloon having proximal and distal ends and an inner chamber which balloon is in fluid communication only with the inflation tube, said balloon disposed in the distal region of the catheter body.

Signed and Sealed this

Twenty-first Day of May, 1996

Attest:

BRUCE LEHMAN

*Attesting Officer*  *Commissioner of Patents and Trademarks*